United States Patent
Karavas et al.

(10) Patent No.: US 10,772,830 B1
(45) Date of Patent: Sep. 15, 2020

(54) PRESERVATIVE FREE PHARMACEUTICAL COMPOSITIONS FOR OPHTHALMIC ADMINISTRATION

(71) Applicants: Evangelos Karavas, Pallini Attikis (GR); Efthimios Koutris, Pallini Attikis (GR); Vasiliki Samara, Pallini Attikis (GR); Ioanna Koutri, Pallini Attikis (GR); Anastasia Kalaskani, Pallini Attikis (GR); Andreas Kakouris, Pallini Attikis (GR); George Gotzamanis, Pallini Attikis (GR)

(72) Inventors: Evangelos Karavas, Pallini Attikis (GR); Efthimios Koutris, Pallini Attikis (GR); Vasiliki Samara, Pallini Attikis (GR); Ioanna Koutri, Pallini Attikis (GR); Anastasia Kalaskani, Pallini Attikis (GR); Andreas Kakouris, Pallini Attikis (GR); George Gotzamanis, Pallini Attikis (GR)

(73) Assignee: PHARMATHEN S.A., Pallini, Attikis (GR)

( * ) Notice: Subject to any disclaimer, the term of this patent is extended or adjusted under 35 U.S.C. 154(b) by 0 days.

(21) Appl. No.: 16/830,883

(22) Filed: Mar. 26, 2020

Related U.S. Application Data

(63) Continuation of application No. 16/405,267, filed on May 7, 2019.

(51) Int. Cl.
| | | |
|---|---|---|
| *A61K 31/5575* | (2006.01) |
| *A61K 47/00* | (2006.01) |
| *A61K 47/12* | (2006.01) |
| *A61K 9/00* | (2006.01) |
| *A61K 47/26* | (2006.01) |
| *A61K 47/10* | (2017.01) |
| *A61K 47/38* | (2006.01) |
| *A61K 9/08* | (2006.01) |
| *A61K 31/165* | (2006.01) |
| *A61K 31/5377* | (2006.01) |
| *A61K 31/382* | (2006.01) |
| *A61K 47/02* | (2006.01) |

(52) U.S. Cl.
CPC .......... *A61K 9/0048* (2013.01); *A61K 9/08* (2013.01); *A61K 31/165* (2013.01); *A61K 31/382* (2013.01); *A61K 31/5377* (2013.01); *A61K 31/5575* (2013.01); *A61K 47/02* (2013.01); *A61K 47/10* (2013.01); *A61K 47/12* (2013.01); *A61K 47/26* (2013.01); *A61K 47/38* (2013.01)

(58) Field of Classification Search
CPC ............ A61K 31/5377; A61K 31/5375; A61K 31/165; A61K 31/382; A61K 47/26; A61K 47/10; A61K 47/12; A61K 47/02; A61K 47/33; A61K 9/00
See application file for complete search history.

(56) References Cited

U.S. PATENT DOCUMENTS

| | | | |
|---|---|---|---|
| 2009/0039048 A1* | 2/2009 | Tien ..................... | A61J 9/04 215/11.5 |
| 2010/0210720 A1* | 8/2010 | Pilotaz ................. | A61P 27/06 514/530 |
| 2011/0319487 A1* | 12/2011 | Mercier ................ | A61K 47/14 514/530 |
| 2012/0312840 A1* | 12/2012 | Hasegawa ............ | A61M 31/00 222/215 |

\* cited by examiner

*Primary Examiner* — Zohreh A Fay
(74) *Attorney, Agent, or Firm* — AKC Patents, LLC; Aliki K. Collins

(57) ABSTRACT

The present invention relates to a preservative-free, aqueous solution in the form of eye drops packed in a container that ensures stability of the product, ideal eye drop volume and reduced drop volume variability and provides efficient dispensing.

6 Claims, No Drawings

PRESERVATIVE FREE PHARMACEUTICAL COMPOSITIONS FOR OPHTHALMIC ADMINISTRATION

CROSS REFERENCE TO RELATED CO-PENDING APPLICATIONS

This application is a continuation and claims the benefit of U.S. application Ser. No. 16/405,267 filed on May 7, 2019 and entitled PRESERVATIVE FREE PHARMACEUTICAL COMPOSITIONS FOR OPHTHALMIC ADMINISTRATION, which is commonly owned and the contents of which are expressly incorporated herein by reference.

TECHNICAL FIELD OF THE INVENTION

The present invention relates to aqueous preservative-free formulations for ophthalmic administration packed in container that ensures physical and chemical stability of the product and provides efficient dispensing.

BACKGROUND OF THE INVENTION

Ocular administration of drugs is primarily associated with the need to treat ophthalmic diseases. The eye is the most easily accessible site for topical administration of a medication. Ophthalmic preparations are sterile products essentially free from foreign particles, suitably compounded and packaged for instillation into the eye. They are easily administered by the nurse or the patient himself, they have quick absorption and effect, less visual and systemic side effects, increased shelf life and better patient compliance.

Drugs may be delivered to the eye through the application of four primary modes of administration: systemic, topical, intravitreal, and periocular. Topical administration is generally considered the preferred route for the administration of ocular drugs due to its convenience and affordability. Drugs applied in this manner can be in multiple forms, including solutions, ointments and suspensions.

Drug absorption occurs through corneal and non-corneal pathways. Most non-corneal absorption occurs via the nasolacrimal duct and leads to non-productive systemic uptake, while most drug transported through the cornea is taken up by the targeted intraocular tissue. Unfortunately, corneal absorption is limited by drainage of the instilled solutions, lacrimation, tear turnover, metabolism, tear evaporation, non-productive absorption/adsorption, limited corneal area, poor corneal permeability, binding by the lacrimal proteins, enzymatic degradation.

The objective of ocular medication delivery is maximizing the amount of medication that reaches the ocular site of action in sufficient concentration to produce a beneficial therapeutic effect. This is determined by the dynamics of ocular pharmacokinetics: absorption, distribution, metabolism and excretion.

Aqueous solutions are most commonly used for the eye. They are the least expensive medications and interfere least with vision. Some commonly used ocular medications are topical anesthetics, mydriatics and cycloplegics, medications used to treat glaucoma, anti-infectives, corticosteroids and non-steroidal anti-inflammatory drugs.

EP 0999825 B1 discloses a topical ophthalmic composition comprising one or more galactomannan(s) and one or more borate compound(s), wherein the galactomannan and the borate compound are contained in the composition in concentrations effective to create a gel or partial gel when the composition is administered to an eye.

U.S. Pat. No. 7,491,383 B2 discloses compositions comprising a therapeutic component and an efficacy enhancing component that enhances the pharmacokinetic disposition of the therapeutic component. The therapeutic component and the efficacy enhancing component may form a complex.

Although each of the patents above represents an attempt to provide stable solutions for ophthalmic administration, there still remains the need in the art for alternative formulations providing as well adequate chemical and physical characteristics and improved patient compliance. In particular, there is a need for formulations that are free from preservatives to be provided in a multiple use container and provide efficient dosing of the solution to the patient, without wastage.

SUMMARY OF THE INVENTION

The present invention aims at developing aqueous pharmaceutical formulations for ophthalmic administration that overcome the disadvantages of and provide significant improvement over the prior art formulations.

It is, therefore, an object of the present invention to provide an efficient ophthalmic product that contains no antimicrobial preservatives. Such product is as effective in terms of therapy as products available with preservatives.

Another object of the present invention is to provide an ophthalmic product that is stable over time at ambient temperature.

A further object of the present invention is to provide an aqueous pharmaceutical formulation for ophthalmic use that effectively addresses issues related to physiological acceptability by patient.

A further approach of the present invention is to provide ophthalmic solutions that are easily administrable in drop form.

In accordance with the above objects of the present invention, eye drops with ideal volume are provided by controlling surface tension of the ophthalmic solution and packing the product in container with appropriate design.

A further aspect of the present invention is to provide reduced drop volume variability in order to obtain higher degree of accuracy and better treatment outcomes.

Other objects and advantages of the present invention will become apparent to those skilled in the art in view of the following detailed description.

DETAILED DESCRIPTION OF THE INVENTION

For the purposes of the present invention, a pharmaceutical composition comprising an active ingredient is considered to be "stable" if said ingredient degrades less or more slowly than it does on its own and/or in known pharmaceutical compositions.

Antimicrobial preservatives are added to aqueous preparations that are required to be sterile, such as in ophthalmic solutions. The use of preservatives in topical ophthalmic treatments is ubiquitous for any product that is to be used more than once by the patient as they prevent any microbes that may enter into the product after its first use from allowing those microbes to grow and infect the patient on a later use of the product. Antimicrobial preservatives are not found in single use vials of ophthalmic solutions since they are manufactured aseptically or are sterilized and the products are used once and the dispenser is thrown away. Although providing effective biocidal properties with well tolerated short-term use at low concentrations, preservatives can cause serious inflammatory effects on the eye with long-term use in chronic conditions, such as glaucoma or potentially ocular allergies.

As the incorporation of preservatives in topical ophthalmic solutions becomes more common, sensitization toward them is increasing. For example, the salts of benzalkonium have been classified as being moderately allergic whereas mercurial products are strongly allergic. Thimerosal may cause ocular delayed hypersensitivity. Chlorhexidine may cause corneal endothelium damage. Parabens are capable of producing immunologically mediated, immediate systemic hypersensitivity reactions.

As the use of preservative containing eye drops has been implicated in the development or worsening of ocular surface disease, there is a tendency to limit their use by reducing their concentration as much as possible in eye drops. The present invention provides completely preservative-free ophthalmic formulations. Such formulations are packed in containers that enable to deliver preservative-free formulations while providing shelf life similar to traditional formulations. The containers of the present invention ensure that medication is kept germ-free even after multiple uses.

Preservative free ophthalmic products are commercially available but these are sold as single use vials made by using a suitable plastic in a blow-fill-seal process. The user takes the plastic vial and tears or cuts the plastic tip, inverts the vial and squeezes the ophthalmic liquid into the eye.

In addition, the use of preservatives is prohibited in ophthalmic products that are used during eye surgery because if the preservative contacts the corneal endothelium the cells can become damaged causing clouding of the cornea and possible loss of vision.

Patient compliance is greatly increased as the pumps of the present invention permit them to use preservative-free eye drops without worrying about the potential side effects caused by some preservatives and the related short- and long-term consequences, such as pain or discomfort, foreign body sensation, stinging or burning, dry eye sensation, ocular surface breakdown.

In addition, we have found that careful selection of certain physical properties of the ophthalmic solution and also the design of the tip of the container produce a highly accurate drop size with low variability of drop volume between each drop dispensed.

Ophthalmic Solutions

The solutions of the present invention are sterile and free from any microbial preservative. Some common ophthalmic drugs suitable for use in this invention include, but are not limited to, chloramphenicol, timolol, dorzolamide, travoprost, bimatoprost, latanoprost, prednisolone, levobunolol, levofloxacin, moxifloxacin, dexamethasone, apraclonidine, bromfenac, epinastine, loteprednol, pegaptanib, prednisolone, pranoprofen, ranibizumab, rimexolone, trafluprost, thiomersal, betaxolol, brimonidine, carteolol, pilocarpine, brinzolamide, apraclonidine, atropine, azelastine, bepotastine, betaxolol, bromfenac, ciprofloxacin, diclofenac, emedastine, epinastine, flurbiprofen, gentamycin, gramicidin, framycetin sulphate, cetrimide, *hamamelis* water, naphazoline, homatropine, ketorolac trometamol, ketotifen fumarate, levobunolol, lodoxamide trometamol, moxifloxacin, naphazoline, pheniramine maleate, nedocromil sodium, ofloxacin, olopatadine, tetracaine, tetrahydrozoline, tobramycin, xylometazoline, antazoline and combinations such as travoprost/timolol, dorzolamide/timolol, bimatoprost/timolol, brimonidine/timolol, latanoprost/timolol, brinzolamide/timolol. Additionally, some ophthalmic solutions have no active ingredient as such but act as a lubricant and are commonly called artificial tears or hypromellose eye drops.

Tonicity refers to the osmotic pressure exerted by salts in aqueous solution. An ophthalmic solution is isotonic with another solution when the magnitudes of the colligative properties of the solutions are equal. An ophthalmic solution is considered isotonic when its tonicity is equal to that of 0.9% sodium chloride solution (290 mOsm). If the tonicity deviates too far from this value, the pain produced evokes a reflex tearing that washes the drug from the eye. Consequently, a certain tonicity agent must be added so that the total osmotic pressure is the same as the body fluid. Sodium chloride, mannitol, dextrose, glycerine, potassium chloride are typical tonicity agents. Isotonicity is desirable and particular important in intraocular solutions. The present invention provides isotonic ophthalmic solutions.

Generally, the tonicity agents bring the osmolality of the solutions to a level at or near 210-320 mOsm/Kg. The ophthalmic compositions of the present invention have an osmolality in the range of 250-300 mOsm/Kg, most preferably in the range of 266-296 mOsm/Kg.

Viscosity is the property of resistance to flow in a fluid or semi fluid. It is an important parameter for ophthalmic compositions. With high viscosity ophthalmic compositions, the liquid drip is poor at the nozzle during extraction from the container, and much of the liquid remains adhering to the area near the outside of the nozzle after the liquid has been dropped. This is undesirable because the remaining liquid can lead to contamination including adhesion of foreign matter, and as a result, the ophthalmic liquid composition can potentially be dropped through a contaminated nozzle at the time of the next use. Particularly in the case of eye drop compositions, excessively poor liquid drip produces a difference in the drop volume, leading to the problem of variation in drug dosage.

The ophthalmic compositions of the present invention have viscosity of less than 200 cP at 25° C., more preferably the viscosity is less than 150 cP at 25° C.

The preferred compositions of the present invention are free of viscosity-increasing agents examples of viscosity increasing agents that are absent include one or more of the following: alginic acid, carrageenan, chitosan, gelatin, guar gum, maltitol, maltodetrin, sucrose, xanthan gum, calcium silicate and sorbitol.

Ophthalmic preparations should be formulated at a pH equivalent to the tear fluid value of 7.4. Practically, this seldom is achieved as the large majority of active ingredients used in ophthalmology are salts of weak bases and are most stable at an acid pH. Optimum pH adjustment generally requires a compromise on the part of the formulator. It is generally accepted that a low pH (acid) per se necessarily will not cause stinging or discomfort on instillation. If the overall pH of the tears, after instillation, reverts rapidly to pH 7.4, discomfort is minimal. On the other hand, if the buffer capacity is sufficient to resist adjustment by tear fluid and the overall eye pH remains acid for an appreciable period of time, then stinging and discomfort may result. Consequently, buffer capacity should be adequate for stability but minimized, so far as possible, to allow the overall pH of the tear fluid to be disrupted only momentarily. A preferred range of pH therefore must be selected according to the active ingredient used.

Preferred compositions are prepared using a buffering system that maintains the composition at a pH of about 5 to a pH of about 8, most preferably 5.5-7.5. Suitable buffering agents include, but are not limited to, dibasic sodium phosphate, monobasic sodium phosphate, hydrochloric acid, sodium hydroxide, sodium hydrogen carbonate.

Surface tension. The actual formation of the drop at the orifice of the tip depends primarily on the surface tension of the solution, assuming the tip is identical. According to Tate's law: $W=mg=2\pi\gamma r$, where W is the weight of the drop, m is the mass of the drop, g is the acceleration of gravity, $\gamma$ is the surface tension of the liquid and r is the radius of the tip. This equation shows that a decrease in the surface tension will reduce the drop weight. The surface tension is affected by the excipients used in formulations.

The present invention provides ophthalmic solutions with lower surface tension. Surface tension is reduced by the addition of surfactants.

Preferred surfactants are nonionic surfactants such as the sorbitan ether esters of oleic acid (polysorbate or Tween® 20 and 80), macrogol glycerol hydroxystearate (cremophor RH-40®), glyceryl monooleate, polyoxyethylene stearates, triethyl citrate.

The concentration of surfactant is preferably at a range of from 0.01% to 2% by weight, more preferably 0.01% to 1% by weight and most preferably 0.01% to 0.5% by weight.

The compositions of the present invention may also comprise other common excipients used in ophthalmic preparations such as antioxidants, salts and/or surfactants.

Common excipients used in ophthalmic compositions are for example borates, mannitol, phosphoric acid, ethyl oleate, propylene glycol, lecithin.

Drop Size

In the Pharmacy field the term "drop" (as a unit) has been standardized to exactly 0.05 ml (so 20 drops equal 1 ml) which abbreviated as "gtt" (or gtts for the plural) coming from gutta, the Latin word for drop. Preferably the drop dispensed is 0.3 to 1.1 gtt, preferably 0.4 to 1.0 gtt and ideally 0.45 to 0.9 gtt.

The average volume of a human tear is 7 µl. The conjunctival sac is capable of holding 20-30 µl of fluid without overflowing onto the cheek; however, the average drop size of commercial topical medications for the eye is around 39 µl. The excess fluid runs to the cheeks or drains to the naso-lacrimal system, where it will be absorbed systemically without first-pass metabolism by liver, and might cause unwanted side effects. One way to overcome this problem is to reduce the size of the drop. In order to obtain eye drops with ideal volume, small-dimension dropper tips are necessary.

The angle at which the dropper bottle is held is another factor which influences the drop size. Dispensing drops from a dropper tip at an angle of 45° from the horizontal significantly decreases the average drop volume. As a result of gravity, tilting from a vertical position to 45° from the horizontal reduces the perimeter of the outer orifice of the dropper tip, at which a drop is formed, and smaller drops would be expected. The weight of a drop is proportional to the radius of the dropper tip according to Tate's law; therefore, a decrease in the drop weight can be obtained when changing the angle from 90° to 450.

A serious problem related to the use of eye drops that are free from preservatives is the considerable degree of imprecision in the dose administered. This is due to the imprecise way in which the dosing tip is formed when plastic vial is torn or cut to remove the tip of the vial as described below. This may be a cause for concern since the pharmacological effect of a compound and the related adverse systemic effects of the drug due to systemic absorption can be greatly influenced by the volume instilled.

Several physical factors of the solution used will be responsible for variation in drop size and these are viscosity and surface tension. In addition, the other factors are those associated with the container and the especially the dispensing tip of the container—assuming that the other factors of the solution are constant such as viscosity and surface tension. The inner diameter and the width of the flat end of the dropper tip and the dispensing angle have been found the most important. The dispensing angle can be fixed—or at least recommended to the patient. Assessment of the repeatability of achieving the correct drop size and of any factors likely to cause increased variation is therefore of great clinical importance.

Drop Size Variability

Drop size variability of the preservative free ophthalmic solutions is reduced in containers of the present invention. The drop volume is in the range of 22-31 µl, most preferably 22.7-30.7 µl when the tip of the nozzle is at 45°, when using ophthalmic solutions described herein.

The variability between each drop dispensed is ±5 µl or expressed as ±0.1 gtt. Ideally the drop variability can be expressed as +15%, ideally ±10% due to some variability id drop size according to the formulation.

Tip

Several dropper tip designs can be distinguished: the simplest design is a nozzle with a small opening for the passage of the liquid; dropper tips with a straight elongated cylindrical channel of uniform cross-section and narrower inner aperture; tips with a conical outward channel below a cylindrical recess channel. Changes in dimension of eye dropper tip can alter drop volumes markedly.

Smaller eye drops are obtained with a tip having the inner diameter that is approximately one-half of the size of the outer diameter.

The flow of the liquid through the dropper tip and the drop size depends on the inner aperture and outer orifice diameter. Preferably there is a constant inner diameter of the dropper tip orifice. In such a system the eye drop size increases linearly with the outer diameter. Dropper tips of the present invention control the size of the drops by control of the inner diameter relative to the outer diameter.

To provide the drop size and drop size variability for the preservative free solution described in the present invention we have found that ideally the dispensing tip should have the following dimensions: the ratio of the inner to the outer diameter of the dispensing tip is from 1:1 to 1:6, preferably from 1:1 to 1:4, most preferably from 1:1 to 1:2.

The inner diameter of the dispensing tip is more than 0.3 mm and less than 2 mm; the outer diameter of the dispensing tip is more than 1 mm and less than 4 mm, wherein the outer diameter is the diameter the tip of the nozzle at the point the drop exits the nozzle and the inner diameter is the diameter of the nozzle at the point the drop exits the nozzle and to which internally the ophthalmic composition moves from the reservoir to the tip.

Therefore, we present as a feature of the present invention a multi-use ophthalmic product comprising a container with an integral bacterial protection system and which has a dispensing tip, wherein the ratio of the inner to the outer diameter of the dispensing tip is from 1:1 to 1:6, and the container having an ophthalmic composition that is dispensed from the tip into the eye of a patient wherein the ophthalmic composition is a preservative-free aqueous solution and contains pharmaceutically acceptable excipients selected so as to provide the following physical parameters to the solution:

a. viscosity of less than 200 cP at 25° C.
b. surface tension of less than 22 mN/m and more than 10 mN/m at 25° C.

wherein the combination of the dispensing tip and the properties of the composition produce a dispensed drop volume of between 22 µl and 31 µl when the tip is at 45°.

Containers

A number of different containers for ophthalmic solutions exist ranging from single use to multiple-use. In the present invention the containers used are multiple-use containers. This means that the device contains more than one dose of ophthalmic solution. Single use products are typically simple blow-fill-seal containers, such as single use glass/plastic ampoules, vials where the tip is removed and the content squeezed into the eye and the container is then discarded. Due to the tip being torn of shorn away then the drop volume is highly variable and the quantity of solution provided is normally largely in excess of that needed. This leads to a lot of wastage in the solution and packaging. This type of product has one major advantage, it is sterile and used only once, therefore, a preservative is not required.

The container volume of the present invention is preferably from 5 to 15 ml, most preferably from 5 to 10 ml.

Preferably the containers are made from glass or plastic materials (e.g. polyethylene, polypropylene, PET). Glass bottles are less prone to give interactions and will give good protection to the formulation even during storage intervals. The disadvantages that glass bottles may have are the higher weight, the risk to break when dropped, the higher costs. On the other hand, bottles made of plastic materials offer increased patient compliance in the case of ophthalmic products as the patient needs only to squeeze the bottle to dispense the product.

Multiple-use containers are widely used and they have the disadvantage in that a preservative system is required. This is due to the danger of bacteria entering into the container and contaminating the solution. There are two pathways for microorganisms to enter the container: a) via the orifice created at the tip and any remaining liquid attached to it coming into contact with infected tears or skin and b) via the venting air where the solution dispensed from the container is replaced by ambient air.

Bacterial Protection Mechanism

In preserved formulations the added preservative controls microbial growth and no additional measures need to be taken to prevent microbial occupation via the orifice or venting air of the container. If the formulation does not contain preservatives, the device must be able to keep microorganisms out of the container to prevent bacteria colonizing the solution inside and requires one or more bacterial protection mechanisms. Newly developed multiple use containers are known that do not require a preservative system since they prevent entry of bacteria into the container due to their special construction and inclusion of germ reducing components. To ensure the microbiological safety of the non-preserved product, such containers are equipped with bacteria protection mechanisms.

Today a range of technical solutions are available to overcome this issue and provide bacterial protection mechanisms. The highest risk of contamination obviously comes from the tip from which the solution exits the container, because it may come in contact with skin and mucosa as well as with infected body fluids. Solutions to prevent contamination via the tip divide into two distinct groups:

1. Containers having "oligodynamic effect" have an open tip that releases metal ions into the formulation that are toxic to bacteria. Examples include the use of silver wire in the tip of the actuator, a silver coated spring and ball. These components release silver ions into the formulation, which is a time dependent process. The system is able to keep microorganisms down between long dosing intervals, even when the tip is immersed into bacterial contaminated fluid. Silver ions are widely used for their antiseptic properties and even when used for wound dressings, it is safe and no adverse effects are attributed to this treatment. One general limitation of course must be considered: the silver ions may react with certain ions in the formulation and may form precipitates—such as with chloride ions.

2. Containers that use a "mechanical effect" to prevent contamination. Typically, this is called "tip seal technology" and is a simple spring-loaded valve located directly below the opening of the tip orifice that does not allow any microbes to migrate from any surfaces or contacted liquids into the system; the orifice is sealed under resting conditions. The tip seal keeps the system closed until a defined pressure is reached then the system will open and the formulation is forced through the orifice with a higher pressure than needed to open the valve. When the pressure drops at the end of the actuation the tip seal will immediately close the orifice with an outward movement. So, no backflow of potentially contaminated medication or other liquid is possible.

Additionally, to protect the integrity of the solution such devices may also have a system to prevent bacteria entering when the system vents. So, after use a negative pressure develops inside the container and air may flow back into the container which may carry air born bacteria. Integrity is achieved by a "mechanical effect" and may be one or more of the following:

1. Collapsible internal bag to contain the solution. The use of an internal collapsible bag to contain the systems avoids any negative pressure developing.

2. Filters, these simply filter the air and trap any air born bacteria

3. Unvented containers—these are containers that do not allow any air to come back into the container at all. Negative pressure continues to build throughout the use of the product without affecting the performance of the container to deliver the solution.

The following examples illustrate preferred embodiments in accordance with the present invention without limiting the scope or spirit of the invention.

EXAMPLES

Example 1

| Ingredients | % w/v |
| --- | --- |
| Travoprost | 0.004 |
| Cremophor RH-40 | 0.200 |
| NaCl | 0.350 |
| Propylene glycol | 0.750 |
| Boric acid | 0.300 |
| Mannitol | 0.300 |
| NaOH/HCl | q.s. pH = 6.0 |
| water for injection | q.s. |

The manufacturing process as followed for the preparation of Composition 1 consists of the following steps:

Adding 80% of the total volume of purified water in a clean vessel of appropriate size;

Adding Propylene glycol and dissolving;

Adding Mannitol, Boric acid and dissolving;

Adding Cremophor RH-40 and stirring till complete dissolution;
Adding NaCl;
Adjusting solution pH to 6 using NaOH or HC 1;
Adding API and stirring until complete API dissolution;
Adjusting solution volume.

Example 2

| Ingredients | % w/v |
| --- | --- |
| Travoprost | 0.004 |
| Timolol maleate | 0.680 |
| Cremophor RH-40 | 0.200 |
| NaCl | 0.350 |
| Propylene glycol | 0.750 |
| Boric acid | 0.300 |
| Mannitol | 0.300 |
| NaOH/HCl | q.s. pH = 6.0 |
| Water for injection | q.s. |

Composition 2 was prepared with the same manufacturing process as in Example 1.

Example 3

| Ingredients | % w/v |
| --- | --- |
| Dorzolamide hydrochloride | 2.226 |
| Mannitol | 2.500 |
| NaOH 0.1 N | qs |
| Sodium Citrate | 0.294 |
| Natrosol HX 250 | 0.570 |
| Water for injection | q.s. |

The manufacturing process as followed for the preparation of Composition 3 consists of the following steps:
Preparation of Solution A
  Adding Mannitol into purified water (which represents about 60% of the total solution volume) and dissolving;
  Adding API and dissolving;
  Adding Sodium citrate and dissolving;
  Adjusting pH to 5.65 by adding the necessary amount of NaOH 0, 1N
  Sterilizing SOLUTION A by filtration through 0.2μηι filter.
Preparation of Solution B
  Adding Natrosol in purified water (which represents about 35% of the total solution volume) and dissolving;
  Autoclaving SOLUTION B for 30 min at 121° C.
Mixing of Solution A and Solution B
  Mixing cool SOLUTION A and cool SOLUTION B;
  Adjusting solution volume using water for injection.

Example 4

| Ingredients | % w/v |
| --- | --- |
| Dorzolamide hydrochloride | 2.226 |
| Timolol maleate | 0.683 |
| Mannitol | 1.600 |
| NaOH 0.1 N | q.s. |
| Sodium Citrate | 0.294 |
| Natrosol HX 250 | 0.580 |
| Water for injection | q.s. |

Composition 4 was prepared with the same manufacturing process as in Example 3.

Drop Sizes Achieved

| COMPOSITIONS | PH | VISCOSITY (cP) | OSMOLALITY (mOsm/Kg) | SPECIFIC GRAVITY | SURFACE TENSION (mN/m) | Drop Volume (μL) |
| --- | --- | --- | --- | --- | --- | --- |
| Travoprost | 6.30 | 0.9-1.1 | 280 | 1.018 | 12.00-13.00 | 22.7-29.3 |
| Travoprost-Timolol | 6.30 | 0.9-1.1 | 286 | 1.007 | 12.00-13.00 | 22.7-29.3 |
| Dorzolamide | 5.67 | 124-138 | 285 | 1.020 | 19.34 | 30.7-41.3 |
| Dorzolamide-Timolol | 5.66 | 135-150 | 276 | 1.020 | 19.21 | 30.2-39.8 |
| Timolol | 7.03 | 0.9-1.1 | 296 | 1.016 | 20.11 | 28.3-36.8 |
| Chloramphenicol | 7.29 | 0.9-1.1 | 281 | 1.011 | 21.22 | 29.6-40.5 |
| Birnatoprost | 7.31 | 0.9-1.1 | 287 | 1.007 | 17.11 | 26.3-34.8 |

The pH, viscosity, osmolality, specific gravity, surface tension and drop volume of compositions prepared according to the present invention were measured via certified methods.

The pH of the compositions was measured according to European pharmacopoeia requirements (Potentiometric determination of pH; 01/2005:20203).

The viscosity of the compositions was measured according to European pharmacopoeia requirements (Capillary viscometer method; 01/2005:20209 or Rotating viscometer method; 01/2005:20210).

The osmolality of the compositions was measured according to European pharmacopoeia requirements (Osmolality; 01/2005:20235).

The specific gravity of the compositions was measured according to US pharmacopoeia requirements (Specific gravity; USP29/841).

The surface tension of the compositions was measured via Kruss DSAIS easy drop tensiometer.

The drop volume of the compositions was measured by measuring the weight of individual drops using an analytical balance and then dividing by the solution density.

The results of drop volume incorporate measurements both from vertical position and from 450 angle. The smallest average drop volume was achieved at an angle of 45° from the horizontal. The drop volume for each product was tested and found to vary by not more than ±5 μL.

TABLE 2

Surface tension measurements

PRESERVATIVE FREE PRODUCTS

| COMPOSITIONS | SURFACE TENSION (mN/m) | DROP VOLUME (μl) |
|---|---|---|
| Dorzolamide | 11.39-11.45 | 22.47-22.58 |
| Dorzolamide/Timolol | 11.09-11.27 | 21.07-21.21 |
| Timolol | 13.08-13.74 | 21.54-23.85 |
| Chloramphenicol | 15.75-16.04 | 34.28-35.20 |
| Bimatoprost | 13.92-14.24 | 23.91-26.13 |

The container used for the compositions comprising Travoprost and Travoprost/Timolol ensures microbiological safety by incorporating germ-reducing components containing oligodynamically active silver.

The container used for the rest of compositions uses the mechanical tip-seal technology to prevent bacterial contamination.

While the present invention has been described with respect to the particular embodiments, it will be apparent to those skilled in the art that various changes and modifications may be made in the invention without departing from the spirit and scope thereof, as defined in the appended claims.

What is claimed is:

1. A multi-use ophthalmic kit comprising:
a container comprising an integral bacterial protection system and a dispensing tip;
an ophthalmic composition contained within the container and configured to be dispensed as drops from an orifice of the dispensing tip into an eye of a patient;
wherein the dispensing tip orifice geometry comprises a ratio of an inner diameter to an outer diameter of the dispensing tip orifice from 1:1 to 1:6, wherein the inner diameter of the dispensing tip orifice is more than 0.3 mm and less than 2 mm and the outer diameter of the dispensing tip orifice is more than 1 mm and less than 4 mm, wherein the outer diameter is the diameter of the dispensing tip at a point a drop exits the dispensing tip and the inner diameter is the diameter of the dispensing tip at the point the drop exits the dispensing tip and to which internally the ophthalmic composition moves from the container to the tip;
wherein the ophthalmic composition comprises a preservative-free aqueous solution of travoprost as an active ingredient and pharmaceutically acceptable excipients selected so as to provide the following physical properties to the solution:
a) viscosity of less than 200 cP at 25° C. as measured by European pharmacopoeia requirements
b) surface tension of less than 22 mN/m and more than 10 mN/m at 25° C.
c) osmolality value of 250 to 300 mOsm/Kg;
wherein the ophthalmic composition is free of viscosity increasing agents;
wherein the integral bacterial protection system uses a mechanical tip-seal technology to prevent bacterial contamination and the mechanical tip-seal technology comprises a spring-loaded valve located directly below the dispensing tip orifice; and
wherein the container is configured to dispense drops of the ophthalmic composition having a volume of between 22 μl and 31 μl when the dispensing tip is oriented at an angle of 45° relative to a horizontal axis and wherein variability between each drop dispensed is +7 μl.

2. The ophthalmic kit according to claim 1, wherein the ophthalmic composition comprises a pH value between 5.5 and 7.5 as measured by European pharmacopoeia requirements.

3. The ophthalmic kit according to claim 1, wherein the osmolality value is from 266 to 296 mOsm/Kg European pharmacopoeia requirements.

4. The ophthalmic kit according to claim 1, wherein the variability between each drop dispensed is +5 μl.

5. The ophthalmic kit according to claim 1, wherein the integral bacterial protection system uses active silver in the dispensing tip orifice as bactericide.

6. A multi-use ophthalmic kit comprising:
a container comprising an integral bacterial protection system and a dispensing tip;
an ophthalmic composition contained within the container and configured to be dispensed as drops from an orifice of the dispensing tip into an eye of a patient;
wherein the dispensing tip orifice geometry comprises a ratio of an inner diameter to an outer diameter of the dispensing tip orifice from 1:1 to 1:6, wherein the inner diameter of the dispensing tip orifice is more than 0.3 mm and less than 2 mm and the outer diameter of the dispensing tip orifice is more than 1 mm and less than 4 mm, wherein the outer diameter is the diameter of the dispensing tip at a point a drop exits the dispensing tip and the inner diameter is the diameter of the dispensing tip at the point the drop exits the dispensing tip and to which internally the ophthalmic composition moves from the container to the tip;
wherein the ophthalmic composition comprises a preservative-free aqueous solution of bimatoprost as an active ingredient and pharmaceutically acceptable excipients selected so as to provide the following physical properties to the solution:
a) viscosity of less than 200 cP at 25° C. as measured by European pharmacopoeia requirements
b) surface tension of less than 22 mN/m and more than 10 mN/m at 25° C.
c) osmolality value of 250 to 300 mOsm/Kg;
wherein the ophthalmic composition is free of viscosity increasing agents;
wherein the integral bacterial protection system uses a mechanical tip-seal technology to prevent bacterial contamination and the mechanical tip-seal technology comprises a spring-loaded valve located directly below the dispensing tip orifice; and
wherein the container is configured to dispense drops of the ophthalmic composition having a volume of between 22 μl and 31 μl when the dispensing tip is oriented at an angle of 45° relative to a horizontal axis and wherein variability between each drop dispensed is +7 μl.

* * * * *